US010433788B2

(12) United States Patent
Boesen

(10) Patent No.: US 10,433,788 B2
(45) Date of Patent: *Oct. 8, 2019

(54) EARPIECE LIFE MONITOR WITH CAPABILITY OF AUTOMATIC NOTIFICATION SYSTEM AND METHOD

(71) Applicant: BRAGI GmbH, München (DE)

(72) Inventor: Peter Vincent Boesen, München (DE)

(73) Assignee: BRAGI GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/048,728

(22) Filed: Jul. 30, 2018

(65) Prior Publication Data

US 2018/0360380 A1 Dec. 20, 2018

Related U.S. Application Data

(63) Continuation of application No. 15/463,462, filed on Mar. 20, 2017, now Pat. No. 10,052,065.
(Continued)

(51) Int. Cl.
*A61B 5/00* (2006.01)
*H04R 1/10* (2006.01)
(Continued)

(52) U.S. Cl.
CPC .......... *A61B 5/6803* (2013.01); *A61B 5/0015* (2013.01); *A61B 5/6817* (2013.01);
(Continued)

(58) Field of Classification Search
CPC ..... H04R 5/033; H04M 1/6058; H04W 4/008
(Continued)

(56) References Cited

U.S. PATENT DOCUMENTS 2,325,590 A   8/1943   Carlisle et al.
2,430,229 A   11/1947  Kelsey
(Continued)

FOREIGN PATENT DOCUMENTS

CN   204244472 U   4/2015
CN   104683519 A   6/2015
(Continued)

OTHER PUBLICATIONS

Stretchgoal—It's Your Dash (Feb. 14, 2014).
(Continued)

*Primary Examiner* — Alexander Jamal
(74) *Attorney, Agent, or Firm* — Goodhue, Coleman & Owens, P.C.

(57) ABSTRACT

An earpiece includes an earpiece housing, at least one biometric sensor disposed within the earpiece, a wireless transceiver disposed within the earpiece for voice communications, an intelligent control operatively connected to the at least one biometric sensor and the wireless transceiver, a speaker operatively connected to the intelligent control, and at least one microphone operatively connected to the intelligent control. The earpiece is configured to monitor biometrics of a user using the at least one biometric sensor, communicate biometric data to the user, detect a crisis level event, and communicate occurrence of the crisis level event using the wireless transceiver.

16 Claims, 5 Drawing Sheets

Related U.S. Application Data

(60) Provisional application No. 62/312,139, filed on Mar. 23, 2016.

(51) Int. Cl.

| | | |
|---|---|---|
| *G10L 13/00* | (2006.01) | |
| *G08B 25/01* | (2006.01) | |
| *G08B 25/10* | (2006.01) | |
| *G08B 21/02* | (2006.01) | |
| *A61B 5/01* | (2006.01) | |
| *A61B 5/021* | (2006.01) | |
| *A61B 5/024* | (2006.01) | |
| *A61B 5/0476* | (2006.01) | |
| *A61B 5/145* | (2006.01) | |

(52) U.S. Cl.
CPC .............. *A61B 5/742* (2013.01); *A61B 5/746* (2013.01); *G08B 25/016* (2013.01); *G08B 25/10* (2013.01); *G10L 13/00* (2013.01); *H04R 1/1016* (2013.01); *H04R 1/1041* (2013.01); *A61B 5/01* (2013.01); *A61B 5/021* (2013.01); *A61B 5/024* (2013.01); *A61B 5/0476* (2013.01); *A61B 5/14532* (2013.01); *A61B 5/14542* (2013.01); *A61B 2560/0242* (2013.01); *G08B 21/02* (2013.01); *H04R 2201/107* (2013.01); *H04R 2420/07* (2013.01)

(58) Field of Classification Search
USPC .................................................. 381/315, 74
See application file for complete search history.

(56) References Cited

U.S. PATENT DOCUMENTS

| | | |
|---|---|---|
| 3,047,089 A | 7/1962 | Zwislocki |
| D208,784 S | 10/1967 | Sanzone |
| 3,586,794 A | 6/1971 | Michaelis |
| 3,696,377 A | 10/1972 | Wall |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| 5,444,786 A | 8/1995 | Raviv |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,689,252 A | 11/1997 | Ayanoglu et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| 5,844,996 A | 12/1998 | Enzmann et al. |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,185,152 B1 | 2/2001 | Shen |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,522,266 B1 | 2/2003 | Soehren et al. |
| 6,542,721 B2 | 4/2003 | Boesen |
| 6,560,468 B1 | 5/2003 | Boesen |
| 6,563,301 B2 | 5/2003 | Gventer |
| 6,654,721 B2 | 11/2003 | Handelman |
| 6,664,713 B2 | 12/2003 | Boesen |
| 6,681,176 B2 | 1/2004 | Funk et al. |
| 6,690,807 B1 | 2/2004 | Meyer |
| 6,694,180 B1 | 2/2004 | Boesen |
| 6,718,043 B1 | 4/2004 | Boesen |
| 6,721,657 B2 | 4/2004 | Ford et al. |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| 7,532,901 B1 | 5/2009 | LaFranchise et al. |
| D601,134 S | 9/2009 | Elabidi et al. |
| 7,668,652 B2 | 2/2010 | Spencer et al. |
| 7,825,626 B2 | 11/2010 | Kozisek |
| 7,859,469 B1 | 12/2010 | Rosener et al. |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |

(56) References Cited

U.S. PATENT DOCUMENTS

| | | |
|---|---|---|
| 8,108,143 B1 | 1/2012 | Tester |
| 8,140,357 B1 | 3/2012 | Boesen |
| 8,238,967 B1 | 8/2012 | Arnold et al. |
| 8,253,589 B2 | 8/2012 | Grimm et al. |
| D666,581 S | 9/2012 | Perez |
| 8,300,864 B2 | 10/2012 | Müllenborn et al. |
| 8,406,448 B2 | 3/2013 | Lin et al. |
| 8,430,817 B1 | 4/2013 | Al-Ali et al. |
| 8,436,780 B2 | 5/2013 | Schantz et al. |
| D687,021 S | 7/2013 | Yuen |
| 8,679,012 B1 | 3/2014 | Kayyali |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,229,227 B2 | 1/2016 | Border et al. |
| 9,317,241 B2 | 4/2016 | Tranchina |
| 9,461,403 B2 | 10/2016 | Gao et al. |
| 9,510,159 B1 | 11/2016 | Cuddihy et al. |
| D773,439 S | 12/2016 | Walker |
| D775,158 S | 12/2016 | Dong et al. |
| 9,524,631 B1 | 12/2016 | Agrawal et al. |
| D777,710 S | 1/2017 | Palmborg et al. |
| 9,544,689 B2 | 1/2017 | Fisher et al. |
| D788,079 S | 5/2017 | Son et al. |
| 9,684,778 B2 | 6/2017 | Tharappel et al. |
| 9,711,062 B2 | 7/2017 | Ellis et al. |
| 9,729,979 B2 | 8/2017 | Özden |
| 9,767,709 B2 | 9/2017 | Ellis |
| 9,818,005 B2 | 11/2017 | Yeager et al. |
| 9,821,767 B2 | 11/2017 | Nixon |
| 9,848,257 B2 | 12/2017 | Ambrose et al. |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0102931 A1 | 5/2004 | Ellis et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0197063 A1 | 9/2005 | White |
| 2005/0212911 A1 | 9/2005 | Marvit et al. |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2007/0102009 A1 | 5/2007 | Wong et al. |
| 2007/0239225 A1 | 10/2007 | Saringer |
| 2007/0242834 A1 | 10/2007 | Coutinho et al. |
| 2007/0247800 A1 | 10/2007 | Smith et al. |
| 2007/0269785 A1 | 11/2007 | Yamanoi |
| 2008/0013747 A1 | 1/2008 | Tran |
| 2008/0076972 A1 | 3/2008 | Dorogusker et al. |
| 2008/0090622 A1 | 4/2008 | Kim et al. |
| 2008/0102424 A1 | 5/2008 | Holljes |
| 2008/0146890 A1 | 6/2008 | LeBoeuf et al. |
| 2008/0187163 A1 | 8/2008 | Goldstein et al. |
| 2008/0215239 A1 | 9/2008 | Lee |
| 2008/0253583 A1 | 10/2008 | Goldstein et al. |
| 2008/0254780 A1 | 10/2008 | Kuhl et al. |
| 2008/0255430 A1 | 10/2008 | Alexandersson et al. |
| 2008/0298606 A1 | 12/2008 | Johnson et al. |
| 2008/0318518 A1 | 12/2008 | Coutinho et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0041313 A1 | 2/2009 | Brown |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0182913 A1 | 7/2009 | Rosenblatt et al. |
| 2009/0191920 A1 | 7/2009 | Regen et al. |
| 2009/0226017 A1 | 9/2009 | Abolfathi et al. |
| 2009/0240947 A1 | 9/2009 | Goyal et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2009/0299215 A1 | 12/2009 | Zhang |
| 2009/0303073 A1 | 12/2009 | Gilling et al. |
| 2009/0304210 A1 | 12/2009 | Weisman |
| 2010/0007805 A1 | 1/2010 | Vitito |
| 2010/0033313 A1 | 2/2010 | Keady et al. |
| 2010/0320961 A1 | 2/2010 | Castillo et al. |
| 2010/0075631 A1 | 3/2010 | Black et al. |
| 2010/0106356 A1 | 4/2010 | Trepagnier et al. |
| 2010/0166206 A1 | 7/2010 | Macours |
| 2010/0168075 A1 | 7/2010 | Dahlstrom et al. |
| 2010/0203831 A1 | 8/2010 | Muth |
| 2010/0210212 A1 | 8/2010 | Sato |
| 2010/0285771 A1 | 11/2010 | Peabody |
| 2010/0290636 A1 | 11/2010 | Mao et al. |
| 2011/0018731 A1 | 1/2011 | Linsky et al. |
| 2011/0103609 A1 | 5/2011 | Pelland et al. |
| 2011/0137141 A1 | 6/2011 | Razoumov et al. |
| 2011/0140844 A1 | 6/2011 | McGuire et al. |
| 2011/0140956 A1 | 6/2011 | Henry et al. |
| 2011/0239497 A1 | 10/2011 | McGuire et al. |
| 2011/0286615 A1 | 11/2011 | Olodort et al. |
| 2011/0293105 A1 | 12/2011 | Arie et al. |
| 2012/0057740 A1 | 3/2012 | Rosal |
| 2012/0155670 A1 | 6/2012 | Rutschman |
| 2012/0159617 A1 | 6/2012 | Wu et al. |
| 2012/0162891 A1 | 6/2012 | Tranchina et al. |
| 2012/0163626 A1 | 6/2012 | Booij et al. |
| 2012/0197737 A1 | 8/2012 | LeBoeuf et al. |
| 2012/0235883 A1 | 9/2012 | Border et al. |
| 2012/0309453 A1 | 12/2012 | Maguire |
| 2013/0106454 A1 | 5/2013 | Liu et al. |
| 2013/0154826 A1 | 6/2013 | Ratajczyk |
| 2013/0178967 A1 | 7/2013 | Mentz |
| 2013/0200999 A1 | 8/2013 | Spodak et al. |
| 2013/0204617 A1 | 8/2013 | Kuo et al. |
| 2013/0293494 A1 | 11/2013 | Reshef |
| 2013/0316642 A1 | 11/2013 | Newham |
| 2013/0343585 A1* | 12/2013 | Bennett .............. H04R 25/554 381/315 |
| 2013/0346168 A1 | 12/2013 | Zhou et al. |
| 2014/0002357 A1 | 1/2014 | Pombo et al. |
| 2014/0004912 A1 | 1/2014 | Rajakarunanayake |
| 2014/0010391 A1 | 1/2014 | Ek et al. |

(56) References Cited

U.S. PATENT DOCUMENTS

| | | |
|---|---|---|
| 2014/0014697 A1 | 1/2014 | Schmierer et al. |
| 2014/0020089 A1 | 1/2014 | Perini, II |
| 2014/0072136 A1 | 3/2014 | Tenenbaum et al. |
| 2014/0072146 A1 | 3/2014 | Itkin et al. |
| 2014/0073429 A1 | 3/2014 | Meneses et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0146973 A1 | 5/2014 | Liu et al. |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0237518 A1 | 8/2014 | Liu |
| 2014/0270227 A1 | 9/2014 | Swanson |
| 2014/0270271 A1 | 9/2014 | Dehe et al. |
| 2014/0276227 A1 | 9/2014 | Pérez |
| 2014/0279889 A1 | 9/2014 | Luna |
| 2014/0310595 A1 | 10/2014 | Acharya et al. |
| 2014/0321682 A1 | 10/2014 | Kofod-Hansen et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0036835 A1 | 2/2015 | Chen |
| 2015/0056584 A1 | 2/2015 | Boulware et al. |
| 2015/0110587 A1 | 4/2015 | Hori |
| 2015/0124058 A1 | 5/2015 | Okpeva et al. |
| 2015/0148989 A1 | 5/2015 | Cooper et al. |
| 2015/0181356 A1 | 6/2015 | Krystek et al. |
| 2015/0230022 A1 | 8/2015 | Sakai et al. |
| 2015/0245127 A1 | 8/2015 | Shaffer |
| 2015/0256949 A1 | 9/2015 | Vanpoucke et al. |
| 2015/0264472 A1 | 9/2015 | Aase |
| 2015/0264501 A1 | 9/2015 | Hu et al. |
| 2015/0310720 A1 | 10/2015 | Gettings et al. |
| 2015/0317565 A1 | 11/2015 | Li et al. |
| 2015/0358751 A1 | 12/2015 | Deng et al. |
| 2015/0359436 A1 | 12/2015 | Shim et al. |
| 2015/0364058 A1 | 12/2015 | Lagree et al. |
| 2015/0373467 A1 | 12/2015 | Gelter |
| 2015/0373474 A1 | 12/2015 | Kraft et al. |
| 2015/0379251 A1 | 12/2015 | Komaki |
| 2016/0033280 A1 | 2/2016 | Moore et al. |
| 2016/0034249 A1 | 2/2016 | Lee et al. |
| 2016/0071526 A1 | 3/2016 | Wingate et al. |
| 2016/0072558 A1 | 3/2016 | Hirsch et al. |
| 2016/0073189 A1 | 3/2016 | Lindén et al. |
| 2016/0094550 A1 | 3/2016 | Bradley et al. |
| 2016/0100262 A1 | 4/2016 | Inagaki |
| 2016/0119737 A1 | 4/2016 | Mehnert et al. |
| 2016/0124707 A1 | 5/2016 | Ermilov et al. |
| 2016/0125892 A1 | 5/2016 | Bowen et al. |
| 2016/0140870 A1 | 5/2016 | Connor |
| 2016/0142818 A1 | 5/2016 | Park |
| 2016/0162259 A1 | 6/2016 | Zhao et al. |
| 2016/0209691 A1 | 7/2016 | Yang et al. |
| 2016/0226713 A1 | 8/2016 | Dellinger et al. |
| 2016/0253994 A1 | 9/2016 | Panchapagesan et al. |
| 2016/0324478 A1 | 11/2016 | Goldstein |
| 2016/0352818 A1 | 12/2016 | Han et al. |
| 2016/0353196 A1 | 12/2016 | Baker et al. |
| 2016/0360350 A1 | 12/2016 | Watson et al. |
| 2017/0021257 A1 | 1/2017 | Gilbert et al. |
| 2017/0046503 A1 | 2/2017 | Cho et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0061817 A1 | 3/2017 | Mettler May |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0065228 A1 | 3/2017 | Hirano |
| 2017/0078780 A1 | 3/2017 | Qian et al. |
| 2017/0078785 A1 | 3/2017 | Qian et al. |
| 2017/0096065 A1 | 4/2017 | Katsuno et al. |
| 2017/0100277 A1 | 4/2017 | Ke |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0119318 A1 | 5/2017 | Shay et al. |
| 2017/0127168 A1 | 5/2017 | Briggs et al. |
| 2017/0131094 A1 | 5/2017 | Kulik |
| 2017/0142511 A1 | 5/2017 | Dennis |
| 2017/0146801 A1 | 5/2017 | Stempora |
| 2017/0150920 A1 | 6/2017 | Chang et al. |
| 2017/0151085 A1 | 6/2017 | Chang et al. |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0164890 A1 | 6/2017 | Leip et al. |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0251295 A1 | 8/2017 | Pergament et al. |
| 2017/0251933 A1 | 9/2017 | Braun et al. |
| 2017/0257698 A1 | 9/2017 | Boesen et al. |
| 2017/0258329 A1 | 9/2017 | Marsh |
| 2017/0263236 A1 | 9/2017 | Boesen et al. |
| 2017/0263376 A1 | 9/2017 | Verschueren et al. |
| 2017/0266494 A1 | 9/2017 | Crankson et al. |
| 2017/0273622 A1 | 9/2017 | Boesen |
| 2017/0280257 A1 | 9/2017 | Gordon et al. |
| 2017/0297430 A1 | 10/2017 | Hori et al. |
| 2017/0301337 A1 | 10/2017 | Golani et al. |
| 2017/0361213 A1 | 12/2017 | Goslin et al. |
| 2017/0366233 A1 | 12/2017 | Hviid et al. |
| 2018/0007994 A1 | 1/2018 | Boesen et al. |
| 2018/0008194 A1 | 1/2018 | Boesen |
| 2018/0008198 A1 | 1/2018 | Kingscott |
| 2018/0009447 A1 | 1/2018 | Boesen et al. |
| 2018/0011006 A1 | 1/2018 | Kingscott |
| 2018/0011682 A1 | 1/2018 | Milevski et al. |
| 2018/0011994 A1 | 1/2018 | Boesen |
| 2018/0012228 A1 | 1/2018 | Milevski et al. |
| 2018/0013195 A1 | 1/2018 | Hviid et al. |
| 2018/0014102 A1 | 1/2018 | Hirsch et al. |
| 2018/0014103 A1 | 1/2018 | Martin et al. |
| 2018/0014104 A1 | 1/2018 | Boesen et al. |
| 2018/0014107 A1 | 1/2018 | Razouane et al. |
| 2018/0014108 A1 | 1/2018 | Dragicevic et al. |
| 2018/0014109 A1 | 1/2018 | Boesen |
| 2018/0014113 A1 | 1/2018 | Boesen |

(56) References Cited

U.S. PATENT DOCUMENTS

| | | | |
|---|---|---|---|
| 2018/0014140 A1 | 1/2018 | Milevski et al. |
| 2018/0014436 A1 | 1/2018 | Milevski |
| 2018/0034951 A1 | 2/2018 | Boesen |
| 2018/0040093 A1 | 2/2018 | Boesen |
| 2018/0042501 A1 | 2/2018 | Adi et al. |
| 2018/0056903 A1 | 3/2018 | Mullett |
| 2018/0063626 A1 | 3/2018 | Pong et al. |

FOREIGN PATENT DOCUMENTS

| | | | |
|---|---|---|---|
| CN | 104837094 A | 8/2015 |
| EP | 1469659 A1 | 10/2004 |
| EP | 1017252 A3 | 5/2006 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2008113053 A1 | 9/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014046602 A1 | 3/2014 |
| WO | 2014043179 A3 | 7/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |
| WO | 2016187869 A1 | 12/2016 |

OTHER PUBLICATIONS

Stretchgoal—The Carrying Case for The Dash (Feb. 12, 2014).
Stretchgoal—Windows Phone Support (Feb. 17, 2014).
The Dash + The Charging Case & The BRAGI News (Feb. 21, 2014).
The Dash-A Word From Our Software, Mechanical and Acoustics Team + An Update (Mar. 11, 2014).
Update From BRAGI—$3,000,000—Yipee (Mar. 22, 2014).
Weisiger; "Conjugated Hyperbilirubinemia", Jan. 5, 2016.
Wertzner et al., "Analysis of fundamental frequency, jitter, shimmer and vocal intensity in children with phonological disorders", V. 71, n.5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).
Akkermans, "Acoustic Ear Recognition for Person Identification", Automatic Identification Advanced Technologies, 2005 pp. 219-223.
Alzahrani et al: "A Multi-Channel Opto-Electronic Sensor to Accurately Monitor Heart Rate against Motion Artefact during Exercise", Sensors, vol. 15, No. 10, Oct. 12, 2015, pp. 25681-25702, XP055334602, DOI: 10.3390/s151025681 the whole document.
Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
Bmw, "BMW introduces BMW Connected—The personalized digital assistant", "http://bmwblog.com/2016/01/05/bmw-introduces-bmw-connected-the-personalized-digital-assistant", (Jan. 5, 2016).
BRAGI is on Facebook (2014).

BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From The First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, On Track(May 16, 2015).
BRAGI Update—Beta2 Production and Factory Line(Aug. 20, 2015).
BRAGI Update—Certifications, Production, Ramping Up (Nov. 13, 2015).
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2015).
BRAGI Update—On Track, Design Verification, How It Works and What's Next(Jul. 15, 2015).
BRAGI Update—On Track, On Track and Gems Overview (Jun. 24, 2015).
BRAGI Update—Status On Wireless, Supply, Timeline and Open House@BRAGI(Apr. 1, 2015).
BRAGI Update—Unpacking Video, Reviews On Audio Perform and Boy Are We Getting Close(Sep. 10, 2015).
FARR, Christina: "iPads In Every Hospital: Apple's Plan to Crack The $3 Trillion Health Care Sector", "https://www.fastcompany.com/3069060/artists-and-scientists-are-teaming-with-businesses-and-non-profits-on-gender-concerns" (Mar. 18, 2017).
Healthcare Risk Management Review, "Nuance updates computer-assisted physician documentation solution" (Oct. 20, 2016).
Hoffman, "How to Use Android Beam to Wirelessly Transfer Content Between Devices", (Feb. 22, 2013).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces A Health + Mobility Concept for Wellness In Mobility", Fountain Valley, Californa (2017).
International Search Report & Written Opinion, PCT/EP16/70245 (dated Nov. 16, 2016).
International Search Report & Written Opinion, PCT/EP2016/070231 (dated Nov. 18, 2016).
International Search Report & Written Opinion, PCT/EP2016/070247 (dated Nov. 18, 2016).

(56) References Cited

OTHER PUBLICATIONS

International Search Report & Written Opinion, PCT/EP2016/07216 (dated Oct. 18, 2016).
International Search Report and Written Opinion, PCT/EP2016/070228 (dated Jan. 9, 2017).
Jain A et al: "Score normalization in multimodal biometric systems", Pattern Recognition, Elsevier, GB, vol. 38, No. 12, Dec. 31, 2005, pp. 2270-2285, XP027610849, ISSN: 0031-3203.
Last Push Before The Kickstarter Campaign Ends on Monday 4pm CET (Mar. 28, 2014).
Lovejoy: "Touch ID built into iPhone display one step closer as third-party company announces new tech", "http://9to5mac.com/2015/07/21/virtualhomebutton/" (Jul. 21, 2015).
Nemanja Paunovic et al, "A methodology for testing complex professional electronic systems", Serbian Journal of Electrical Engineering, vol. 9, No. 1, Feb. 1, 2012, pp. 71-80, XPO55317584, YU.
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometirics.html", 4 pages (Jul. 28, 2015).
Staab, Wayne J., et al., "A One-Size Disposable Hearing Aid is Introduced", The Hearing Journal 53(4):36-41) Apr. 2000.

\* cited by examiner

EARPIECE LIFE MONITOR WITH CAPABILITY OF AUTOMATIC NOTIFICATION SYSTEM AND METHOD

PRIORITY STATEMENT

This application is a continuation of U.S. patent application Ser. No. 15/463,462 filed on Mar. 20, 2017 which claims priority to U.S. Provisional Patent Application 62/312,139, filed on Mar. 23, 2016, all of which are titled Earpiece Life Monitor with Capability of Automatic Notification System and Method and all of which are hereby incorporated by reference in their entireties.

FIELD OF THE INVENTION

The present invention relates to wearable devices. More particularly, but not exclusively, the present invention relates to ear pieces.

BACKGROUND

Individuals with chronic debilitating conditions oftentimes face extreme challenges when attempting to live independent lives without significant oversight. Such individuals are frequently presented with challenges the average able-bodied individual cannot comprehend. These include many of the activities of daily living, i.e. bathing, eating and unassisted ambulation throughout their dwelling. While the fully ambulatory individual would not consider these tasks as posing any type of challenge, others are not so lucky. Consequently, there exists a need for a new device able to monitor the biometric levels of the user, communicate data directly to the user, contact secondary care providers or relatives, upload data from the user to a database, alert appropriate personnel in case of sensor data detection of a crisis level event, link to appropriate electronic data systems when emergency medical responders to transfer data regarding the event, and allow the device to access the phone network through voice interfaces so an incapacitated user would be able to place the phone call directly from their position after the event occurrence.

Therefore, what is needed is an improve ear piece which includes a life monitor.

SUMMARY

Therefore, it is a primary object, feature, or advantage of the present invention to improve over the state of the art.

It is a further object, feature, or advantage of the present invention to provide an earpiece which can monitor the biometric levels of the user.

It is a still further object, feature, or advantage of the present invention to provide an earpiece able to communicate data directly to the user.

Another object, feature, or advantage is to provide an earpiece which can contact secondary care providers or relatives.

Yet another object, feature, or advantage is to provide an earpiece which can upload data from the user to a database or remote server.

A further object, feature, or advantage is to alert appropriate personnel in case sensor data detection of a crisis level event.

A still further object, feature, or advantage is to link to appropriate electronic data systems with emergency medical responders to transfer data regarding an event.

Another object, feature, or advantage is to allow a device to access the phone network through voice interfaces, so an incapacitated user would be able to place a phone call directly from their position after an occurrence of an emergency or crisis level event.

One or more of these and/or other objects, features, or advantages of the present invention will become apparent from the specification and following claims. No single embodiment need provide each and every object, feature, or advantage. Different embodiments may have different objects, features, or advantages. Therefore, the present invention is not to be limited to or by an objects, features, or advantages stated herein.

According to one aspect methods and systems for the ongoing monitoring and care of the person suffering from incapacitation are provided. This may be used in settings ranging from in-hospital care and monitoring of the individual in each hospital bed or room to the individual who has been released from the facility to continue their lives in the at-home situation. This new construct may effectively solve the issues currently facing individuals recovering from recent interventions through individuals forced to live with ongoing issues affecting their ability to perform the activities of daily living in their home environments. The in-ear solution provides a robust platform to provide superior service to these individuals and allow them the comfort, safety and enhanced security of an effective biometric monitor and warning system.

According to another aspect, an earpiece includes an earpiece housing, at least one biometric sensor disposed within the earpiece, a wireless transceiver disposed within the earpiece for voice communications, a processor operatively connected to the at least one biometric sensor and the wireless transceiver, a speaker operatively connected to the processor, and at least one microphone operatively connected to the processor. The earpiece is configured to monitor biometrics of a user using the at least one biometric sensor, communicate biometric data to the user, detect a crisis level event, and communicate occurrence of the crisis level event using the wireless transceiver. The earpiece may be further configured to upload the biometric data to a database associated with a remote server. The earpiece may be configured to communicate the biometric data to the user through voice feedback. The earpiece may be configured to communicate the biometric data to the user by interacting with a mobile device in operative communication with the earpiece, the mobile device having a display so as to display the biometric data on the display of the mobile device. The earpiece may be configured to communicate occurrence of the crisis level event by initiating a voice call to a third party. The earpiece may be configured to communicate occurrence of the crisis level event by sending an indicator of the crisis level event to a remote server.

According to another aspect, a method for monitoring an individual suffering from at least partial incapacitation is provided. The method includes providing an earpiece comprising an earpiece housing, at least one biometric sensor disposed within the earpiece, a wireless transceiver disposed within the earpiece for voice communications, a processor operatively connected to the at least one biometric sensor and the wireless transceiver, a speaker operatively connected to the processor, and at least one microphone operatively connected to the processor. The method further includes monitoring biometrics of a user of the earpiece using the at least one biometric sensor, detecting a crisis level event using the biometrics, and wirelessly communicating an alert associated with the crisis level event from the earpiece to a remote location using the wireless transceiver. The method may further include communicating the biometrics of the user of the earpiece to the user. The communicating of the biometrics may include the step of generating speech describing the biometrics of the user of earpiece at a speaker of the earpiece. The communicating of the biometrics may include communicating the biometric data to the user by interacting with a mobile device in operative communication with the earpiece, the mobile device having a display so as to display the biometric data on the display of the mobile device. The step of wirelessly communicating the alert associated with the crisis level event from the earpiece to the remote location using the wireless transceiver may include accessing a mobile device in operative communication with the earpiece and initiating a voice call using the mobile device.

According to another aspect, a system includes an earpiece comprising (a) an earpiece housing, (b) at least one biometric sensor disposed within the earpiece, (c) a wireless transceiver disposed within the earpiece for voice communications, (d) a processor operatively connected to the at least one biometric sensor and the wireless transceiver, (e) a speaker operatively connected to the processor, and (f) at least one microphone operatively connected to the processor. The system may further include a software application executing on a mobile device in operative communication with the earpiece. The earpiece may be configured to monitor biometrics of a user using the at least one biometric sensor, communicate biometric data to the software application executing on the mobile device. The earpiece may be configured to detect a crisis level event by analyzing the biometric data. The earpiece may be configured to communicate occurrence of the crisis level to the mobile device.

DETAILED DESCRIPTION

The present invention in some respects provides for the ongoing monitoring and care of a person suffering from incapacitation. This may be used in a variety of different settings including in-hospital care and monitoring of each individual in each hospital bed or room to the individual who has been released from the facility to continue their lives in the at-home situation. This new construct may effectively solve the issues currently facing individuals recovering from recent interventions through individuals forced to live with ongoing issues affecting their ability to perform the activities of daily living in their home environments. The in-ear solution provides a robust platform to provide superior service to these individuals and allow them the comfort, safety and enhanced security of an effective biometric monitor and warning system.

Figure 1:
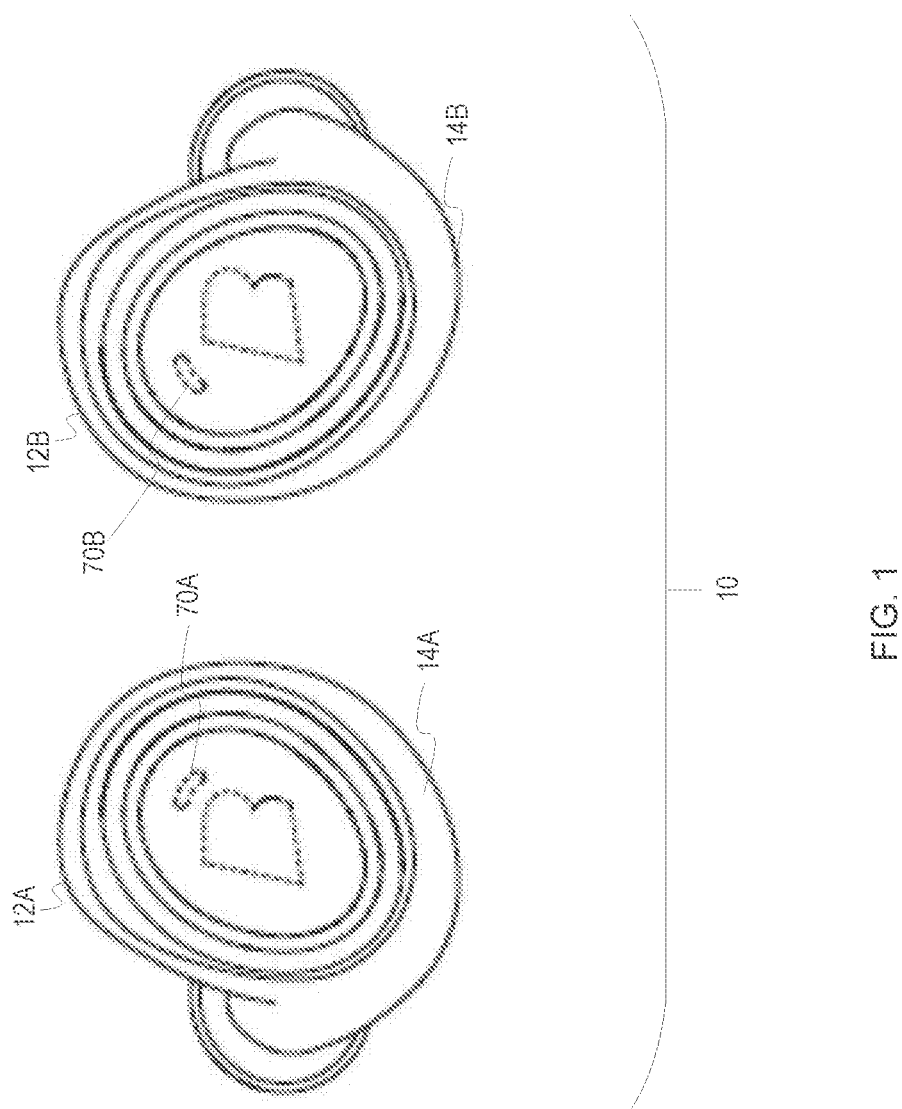
FIG. 1 illustrates a set of earpieces including a left earpiece and a right earpiece.

FIG. 1 illustrates a set of earpieces 10 including a left earpiece 12A and a right earpiece 12B. The left earpiece 12A has a housing or casing 14A and the right earpiece 12B has a housing or casing 14B. A microphone 70A is shown on the left earpiece 12A and a microphone 70B is shown on the right earpiece 12B.

Figure 2:
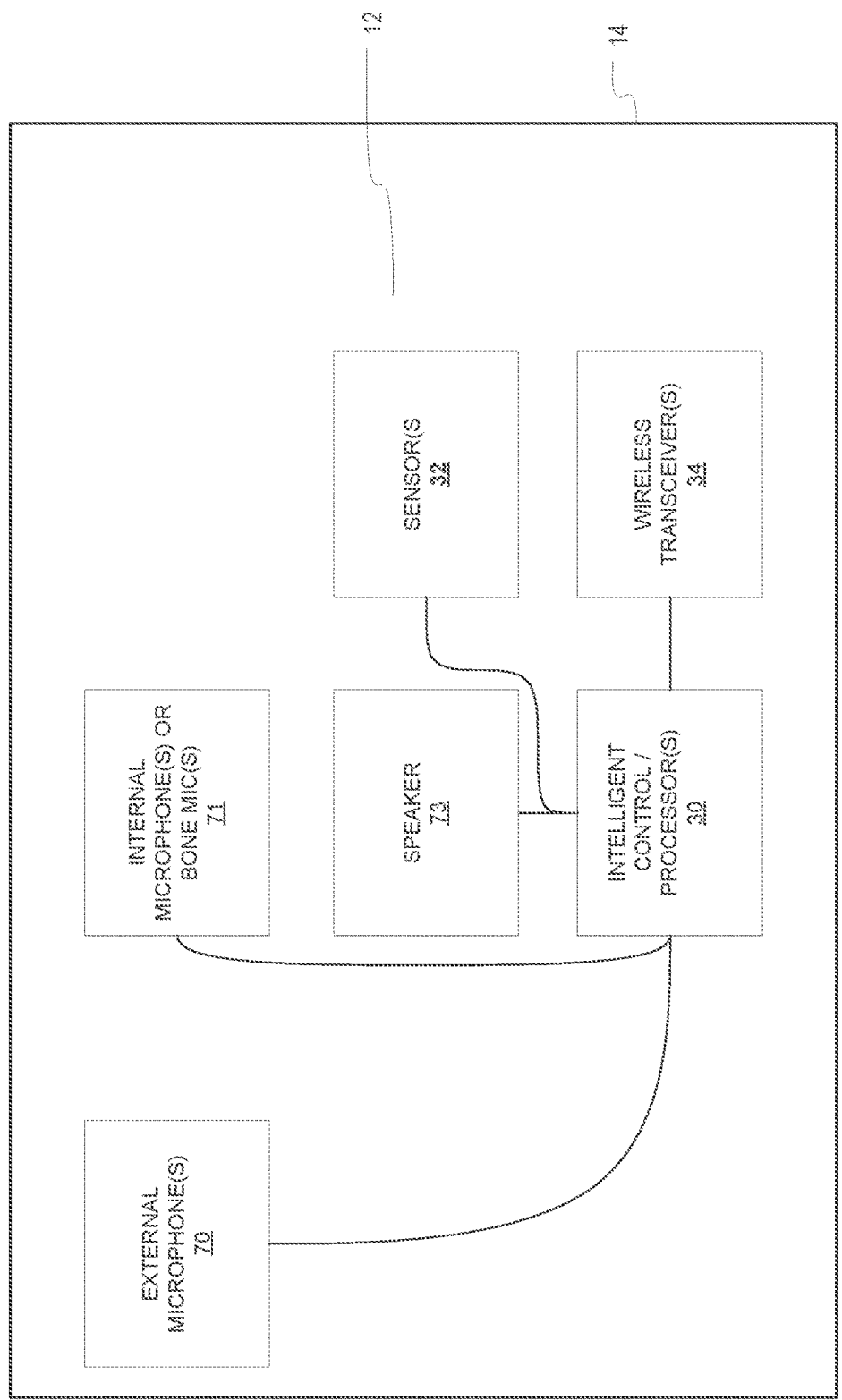
FIG. 2 is a block diagram of one example of an earpiece.

FIG. 2 illustrates an earpiece 12 which may be a left earpiece or a right earpiece. One or more processors or other intelligent control 30 are shown disposed within the housing 14 of the earpiece. One or more wireless transceivers 34 are operatively connected to the intelligent controls 30. The term "processor" as used herein means a single processor or more than one processor in operative communication. The processor or intelligent control 30 may include a digital signal processor, a microprocessor, both, and/or other types of processors. The wireless transceivers 34 may include a BLUETOOTH transceiver, an ultra-wideband (UWB) transceiver, or type of radio transceiver, a near field magnetic induction (NFMI) transceiver, or other type of transceiver. One or more external microphones 70 is/are operatively connected to the processor 30 as are one or more internal microphones or bone microphones 71. One or more sensors 32, including biological or physiological or other biometric sensors may be operatively connected to the processor 30.

Figure 3:
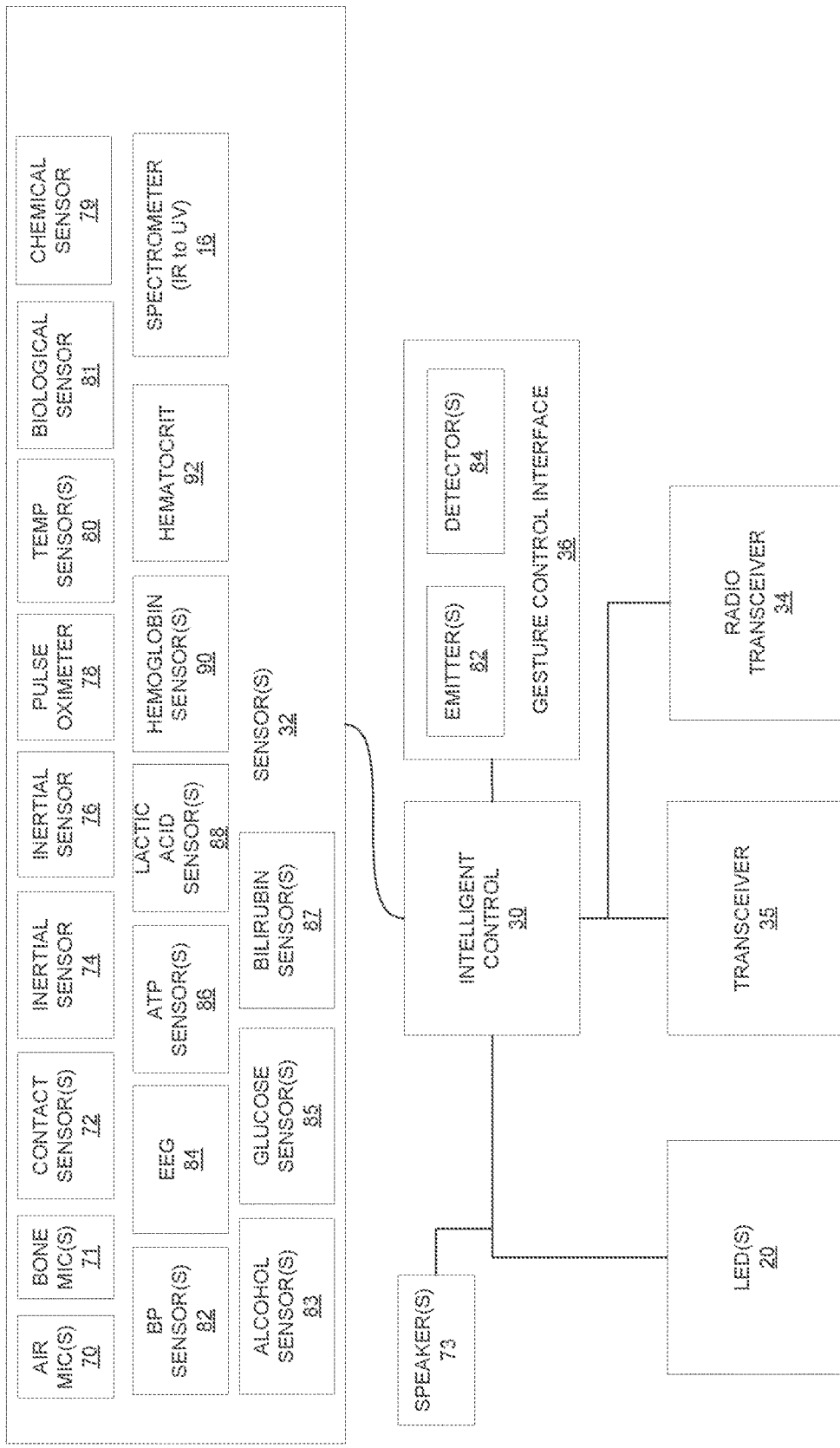
FIG. 3 is a block diagram of another example of an earpiece.

FIG. 3 is a block diagram illustrating a device. The device may include one or more LEDs 20 electrically connected to an intelligent control 30. The intelligent control system 30 may include one or more processors, microcontrollers, application specific integrated circuits, or other types of integrated circuits. The intelligent control 30 may also be electrically connected to one or more sensors 32. Where the device is an earpiece, the sensor(s) may include an inertial sensor 74 and another inertial sensor 76. Each inertial sensor 74, 76 may include an accelerometer, a gyro sensor or gyrometer, a magnetometer or other type of inertial sensor. The sensor(s) 32 may also include one or more contact sensors 72, one or more bone conduction microphones 71, one or more air conduction microphones 70, one or more chemical sensors 79, a pulse oximeter 76, a temperature sensor 80, or other physiological or biological sensor(s). Further examples of physiological or biological sensors include an alcohol sensor 83, glucose sensor 85, or bilirubin sensor 87. Other examples of physiological or biological sensors may also be included in the device. These may include a blood pressure sensor 82, an electroencephalogram (EEG) 84, an Adenosine Triphosphate (ATP) sensor, a lactic acid sensor 88, a hemoglobin sensor 90, a hematocrit sensor 92 or other biological or chemical sensor.

A spectrometer 16 is also shown. The spectrometer 16 may be an infrared (IR) through ultraviolet (UV) spectrometer although it is contemplated any number of wavelengths in the infrared, visible, or ultraviolet spectrums may be detected. The spectrometer 16 is preferably adapted to measure environmental wavelengths for analysis and recommendations and thus preferably is located on or at the external facing side of the device.

A gesture control interface 36 is also operatively connected to or integrated into the intelligent control system 30. The gesture control interface 36 may include one or more emitters 82 and one or more detectors 84 for sensing user gestures. The emitters may be of any number of types including infrared LEDs. It is contemplated instead of being light based, the gesture control interface 36 may be capacitance based instead. The device may include a transceiver 35 which may allow for induction transmissions such as through near field magnetic induction. A short range transceiver 34 using Bluetooth, BLE, UWB, or other means of radio communication may also be present. The short range transceiver 34 may be used to communicate with the vehicle control system. In operation, the intelligent control 30 may be configured to convey different information using one or more of the LED(s) 20 based on context or mode of operation of the device. The various sensors 32, the intelligent control 30, and other electronic components may be located on the printed circuit board of the device. One or more speakers 73 may also be operatively connected to the intelligent control 30.

A magnetic induction electric conduction electromagnetic (E/M) field transceiver 37 or other type of electromagnetic field receiver is also operatively connected to the intelligent control system 30 to link the processor 30 to the electromagnetic field of the user. The use of the E/M transceiver 37 allows the device to link electromagnetically into a personal area network or body area network or other device. Although various types of biometric sensors are shown and described, it is contemplated one or more other sensors may be present. It is to be understood any number of biometric sensors may be present including fewer or more than what is shown in FIG. 3. It is further contemplated where multiple earpieces are used, a first or left earpiece may include a first subset of the sensors 32 and a second or right earpiece may include a second subset of the sensors 32.

Figure 4:
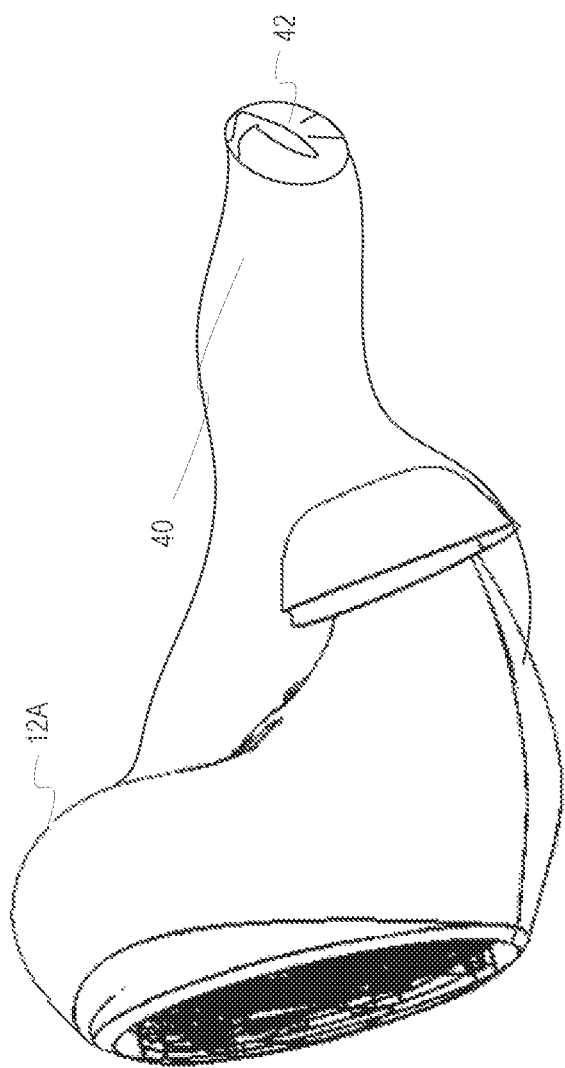
FIG. 4 illustrates one example of an earpiece fitted to an external auditory canal of a user.

FIG. 4 illustrates one example of an earpiece 12A positioned within an external auditory canal of a user. A tympanic membrane 42 is shown at the inner end of the external auditory canal 40. The earpiece may be used to perform any number of different types of sensing at or proximate to the ear of a user.

Figure 5:
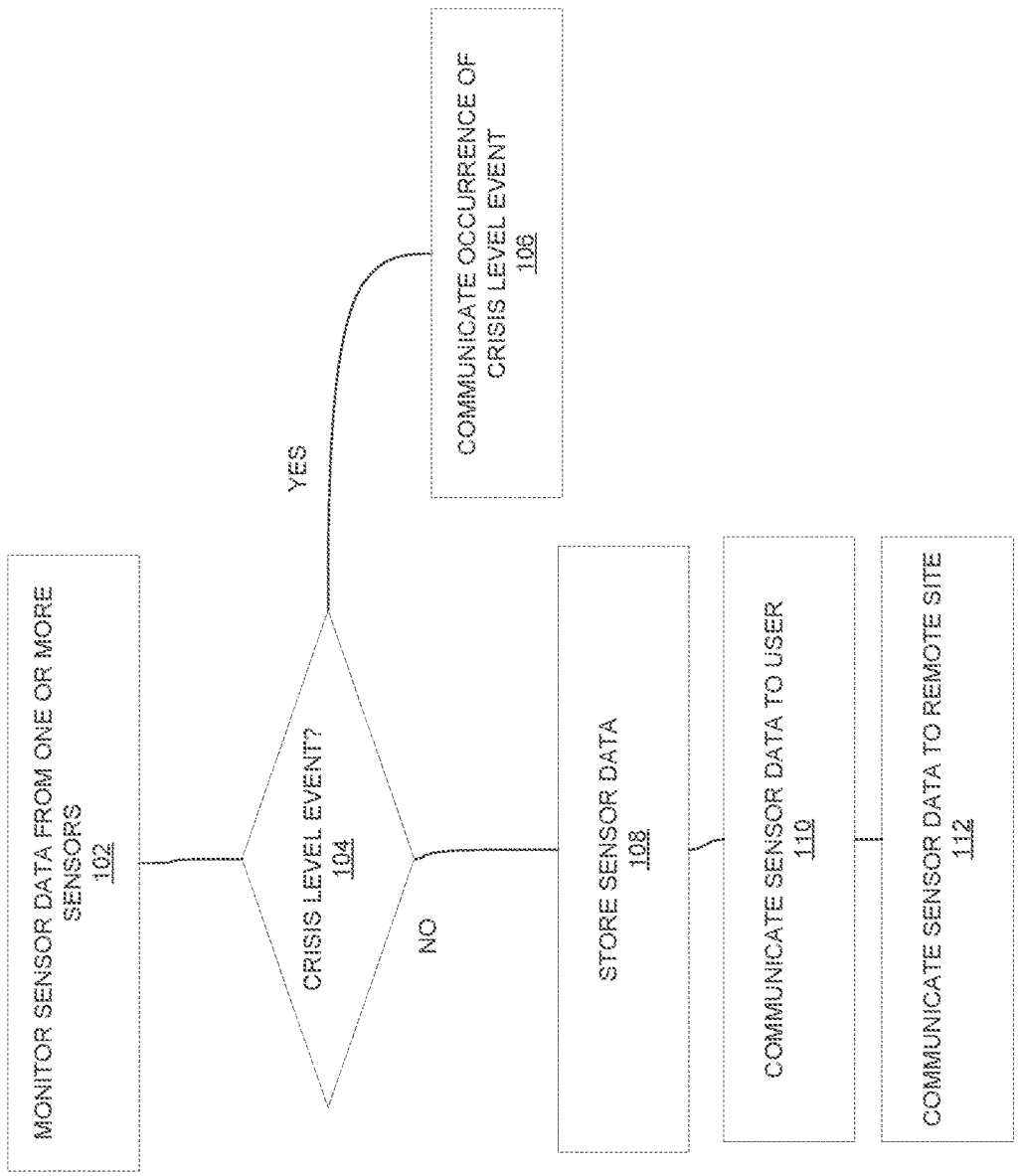
FIG. 5 is a flow diagram illustrating one example of a methodology.

FIG. 5 illustrated on example of a methodology according to another aspect. In step 102 sensor data from one or more sensors of one or more earpieces is monitored. In step 104 a determination may be made such as by the intelligent control system 30 of the earpiece as to whether or not a crisis level event has occurred. This determination may be performed in various ways. In one example, the determination is made by comparing a sensor reading to a threshold level associated with a crisis level event. If the sensor level crosses the threshold level than the device determines a crisis level event has occurred.

In another example, a determination a crisis level event has occurred only happens when the sensor readings cross the threshold for several consecutive readings or for an amount of time. Determining the occurrence of a crisis level event in this manner reduces likelihood of falsely identifying an event as a crisis level event.

Regardless of the manner in which the determination is made, if there is a crisis level event, then in step 106 the occurrence of the crisis level event may be communicated to the user, to emergency contacts, to emergency personnel, or others. If there is no crisis level event then in normal operation, the sensor data may be stored in step 108, the sensor data may communicate to a user in step 110, and the sensor data may be communicated to a remote site in step 112. These steps may occur in various ways. For example, the earpiece may be configured to upload the biometric data to a database associated with a remote server. In addition, the earpiece may be configured to communicate the biometric data to a user in any number of ways. For example, the earpiece may be configured to communicate the biometric data to the user through voice feedback. Thus, for example, when prompted by the user, periodically according to user preferences, or when a particular threshold is crossed, the earpiece may perform speech processing and speak the relevant data such as heat rate, glucose level, temperature, etc. Alternatively, the one or more earpieces may interact with a mobile device in operative communication therewith. The display of the mobile device may be used as a display to display biometric data collected from the earpiece. It should be understood the mobile device may be a mobile device of a person wearing the earpiece or may be a different mobile device. Thus, for example, a patient who checks into a hospital may be assigned one or more earpieces to wear and a mobile device such as a tablet computer. The earpieces may communicate with the tablet computer which may be in operative communication with other hospital systems.

Returning to step 106, the occurrence of the crisis level event may be communicated to the user, to emergency contacts, to emergency personnel, or others. This may occur in various ways. For example, the earpiece may initiate a voice call to a third party. For example, the earpiece may be in operative communication with a mobile device such as a smart phone and initiate a voice call to a third party such as an emergency contact of the individual wearing the earpiece, an emergency service such as 911, a private health monitoring company, a nurse's station, a health care provider, or other individual. The person being monitored may then communicate with the third party. Thus, for example, third party may then ask the person being monitored if they are all right or ask them for relevant information. If data is being logged to a remote site the third party has access to, the third party may then check the data on the remote site to provide them with additional information regarding the situation. The earpiece may also provide for speech processing to communicate the alert verbally to the third party which may be useful if the person being monitored is non-verbal or unable to respond. The earpiece may also directly prompt the user if they are all right such as providing a voice prompt and asking the user to respond using voice or respond by using the gestural interface of the earpiece and tap, double tap, triple tap, swipe, or otherwise provide user input to the earpiece.

The third party may be notified in other ways as well. For example, wherein the earpiece is configured to communicate occurrence of the crisis level event by sending an indicator of the crisis level event to a remote server. The remote server may then make a phone call, send a text message, send an email, send a social media or application specific notification, or otherwise provide a notification or alert.

It should also be understood the earpiece may include an earpiece identifier which identifies the earpiece and/or the person wearing the earpiece. Thus, an identity of the person wearing the earpiece may also be communicated along with the sensor data.

Therefore, various methods, systems, and apparatus have been shown and described. The present invention contemplates numerous options, variation, and alternatives and is not to be limited to the specific embodiments shown herein.

What is claimed is:

1. A set of wireless earpieces comprising a first wireless earpiece and a second wireless earpiece:
   the first wireless earpiece comprising:
   an earpiece housing;
   at least one biometric sensor disposed within the first wireless earpiece;
   a wireless radio transceiver disposed within the first wireless earpiece for voice communications;
   an intelligent control, disposed within the first wireless earpiece, operatively connected to the at least one biometric sensor and the wireless radio transceiver;
   a transceiver operatively connected to the intelligent control for operative communication with the second wireless earpiece;
   a speaker operatively connected to the intelligent control;

an inertial sensor operatively connected to the intelligent control;
at least one microphone operatively connected to the intelligent control;
the second wireless earpiece comprising:
at least one biometric sensor disposed within the second earpiece;
an intelligent control within the second wireless earpiece and operatively connected to the at least one biometric sensor;
a transceiver operatively connected to the intelligent control for operative communication with the first wireless earpiece;
a speaker operatively connected to the intelligent control;
an inertial sensor operatively connected to the intelligent control;
at least one microphone operatively connected to the intelligent control;
wherein the set of wireless earpieces is configured to monitor biometrics of a user using the at least one biometric sensor of the first wireless earpiece and the at least one biometric sensor of the second wireless earpiece to provide biometric data, monitor inertial changes of the user using the inertial sensor of the first wireless earpiece and the inertial sensor of the second wireless earpiece, communicate the biometric data and the inertial data to the user, prompt the user to determine if the user is all right using a voice prompt, detect a crisis level event, and communicate occurrence of the crisis level event to a remote location using the wireless transceiver of the first or second earpieces;
wherein the set of wireless earpieces is configured to, upon detection of the crisis level event, initiate a voice call to communicate the crisis level event through the transceiver of the first or second earpieces to appropriate personnel, such as emergency contacts of the user and or emergency personnel and wherein the crisis level event is communicated by performing speech processing by the set of wireless earpieces to verbally communicate the crisis level event.

2. The set of wireless earpieces of claim 1, wherein the set of wireless earpieces is further configured to upload the biometric data to a database associated with a remote server.

3. The set of wireless earpieces of claim 1, wherein the set of wireless earpieces is configured to communicate the biometric data to the appropriate personnel through voice feedback.

4. The set of wireless earpieces of claim 1, wherein the set of wireless earpieces is configured to communicate occurrence of the crisis level event by initiating a voice call to a third party.

5. The set of wireless earpieces of claim 1 wherein the set of wireless earpieces is configured to communicate occurrence of the crisis level event by sending an indicator of the crisis level event to a remote server.

6. A method for monitoring an individual suffering from at least partial incapacitation, the method comprising steps of:
assigning a set of wireless earpieces to an individual once the individual is admitted to a health care facility;
wherein the set of wireless earpieces includes a first earpiece and a second earpiece; he first earpiece comprising:
a first earpiece housing;
at least one biometric sensor disposed within the first earpiece housing;
a wireless radio transceiver disposed within the first earpiece housing for voice communications;
an intelligent control operatively connected to the at least one biometric sensor and the wireless radio transceiver;
a speaker operatively connected to the intelligent control;
at least one microphone operatively connected to the intelligent control,
an inertial sensor operatively connected to the intelligent control, and
a transceiver operatively connected to the intelligent control for communication with the second earpiece;
wherein the second earpiece comprises:
a second earpiece housing;
at least one biometric sensor disposed within the second earpiece housing;
a speaker;
at least one microphone;
an intelligent control operatively connected to the at least one biometric sensor to the speaker and the at least one microphone;
an inertial sensor operatively connected to the intelligent control; and
a transceiver operatively connected to the intelligent control for communication with the first earpiece;
monitoring biometric data and inertial data of a user of the set of wireless earpieces using the at least one biometric sensor of the first earpiece, the at least one biometric sensor of the second earpiece, the inertial sensor of the first earpiece and an inertial sensor of the second earpiece;
detecting a crisis level event when the at least one biometric sensor and or the inertial sensor provide a reading exceeding a threshold level associated with the crisis level event prompting the user to determine if the user is all right using a voice prompt;
notifying authorized personnel of the crisis level event by initiating a voice call to communicate the crisis level event through the transceiver; and
wirelessly communicating an alert associated with the crisis level event from the set of wireless earpieces to a remote location using the wireless radio transceiver of the first earpiece wherein the crisis level event is communicated by performing speech processing by the set of wireless earpieces to verbally communicate the crisis level event.

7. The method of claim 6, further comprising communicating the biometric data of the user of the set of wireless earpieces to the authorized personnel.

8. The method of claim 7, wherein the communicating the biometric data of the user of the set of wireless earpieces to the authorized personnel comprises generating speech describing the biometric data of the user of the set of wireless earpieces at a speaker of the set of wireless earpieces.

9. The method of claim 8, wherein the communicating the biometric data of the user of the set of wireless earpieces to the authorized personnel comprises communicating the biometric data to the authorized personnel by interacting with a mobile device in operative communication with the set of wireless earpieces, the mobile device having a display, so the biometric data can be displayed of the mobile device.

10. The method of claim 9, wherein the mobile device is a tablet computer.

11. The method of claim 6, wherein the wirelessly communicating the alert associated with the crisis level event from the set of wireless earpieces to the remote location using the wireless radio transceiver comprises accessing a mobile device in operative communication with the earpiece and initiating a voice call using the mobile device.

12. The method of claim 6, wherein the step of detecting the crisis level further comprises at least one of crossing the threshold a preset number of consecutive sensor readings and crossing a predetermined threshold for a preset amount time.

13. The method of claim 6, wherein the first earpiece further comprises a gestural interface operatively connected to the intelligent control of the first earpiece.

14. A system comprising:
a set of wireless earpieces comprising of a first wireless earpiece and a second wireless earpiece;
the first wireless earpiece comprising:
(a) an earpiece housing;
(b) at least one biometric sensor disposed within the first wireless earpiece;
(c) a wireless radio transceiver disposed within the first wireless earpiece for voice communications;
(d) an intelligent control operatively connected to the at least one biometric sensor and the wireless radio transceiver;
(e) a speaker operatively connected to the intelligent control;
(f) at least one microphone operatively connected to the intelligent control;
(g) an inertial sensor operatively connected to the intelligent control; and
(h) a transceiver operatively connected to the intelligent control for communication with the second earpiece;
the second wireless earpiece comprising:
(a) an earpiece housing;
(b) at least one biometric sensor disposed within the second earpiece;
(c) an intelligent control operatively connected to the at least one biometric sensor;
(d) a speaker operatively connected to the intelligent control;
(e) at least one microphone operatively connected to the intelligent control;
(f) an inertial sensor operatively connected to the intelligent control; and
(g) a transceiver operatively connected to the intelligent control for communication with the first earpiece;
a software application executing on a mobile device in operative communication with the set of wireless earpieces;
wherein the set of wireless earpieces is configured to monitor biometric data of a user using the at least one biometric sensor of the first wireless earpiece and the at least one biometric sensor of the second wireless earpiece, monitor inertial data of the user using the inertial sensor of the first wireless earpiece and the inertial sensor of the second wireless earpiece, and communicate the biometric data and the inertial data to the software application executing on the mobile device;
wherein the set of wireless earpieces is configured to detect a crisis level event by analyzing the biometric data and or the inertial data, prompting the user to determine if the user is all right using a voice prompt, and initiating a voice call to communicate occurrence of the crisis level event to a remote location using the wireless transceiver;
wherein the set of wireless earpieces is configured to confirm the crisis level event by providing a direct voice prompt from the set of wireless earpieces requesting authorized personnel provide input to the set of wireless earpieces, and wherein the crisis level event is communicated by performing speech processing by the set of wireless earpieces to verbally communicate the crisis level event;
wherein the set of wireless earpieces is further configured to communicate occurrence of the crisis level to the mobile device.

15. The system of claim 14, wherein the mobile device is a tablet computer.

16. The system of claim 15 wherein the mobile device is a phone.

* * * * *